US010053401B1

(12) United States Patent
Beadle et al.

(10) Patent No.: US 10,053,401 B1
(45) Date of Patent: Aug. 21, 2018

(54) PROCESS FOR RECOVERY OF LIGHT ALKYL MONO-AROMATIC COMPOUNDS FROM HEAVY ALKYL AROMATIC AND ALKYL-BRIDGED NON-CONDENSED ALKYL AROMATIC COMPOUNDS

(71) Applicant: Saudi Arabian Oil Company, Dhahran (SA)

(72) Inventors: Bruce Richard Beadle, Dhahran (SA); Vinod Ramaseshan, Ras Tanura (SA); Rakan Sulaiman Bilaus, Dhahran (SA); Omer R. Koseoglu, Dhahran (SA); Robert P. Hodgkins, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 15/435,039

(22) Filed: Feb. 16, 2017

(51) Int. Cl.
*C07C 4/12* (2006.01)
*C07C 4/14* (2006.01)
*C07C 4/18* (2006.01)
*C07C 4/24* (2006.01)

(52) U.S. Cl.
CPC ............ *C07C 4/24* (2013.01); *C07C 2529/16* (2013.01)

(58) Field of Classification Search
CPC ............... C07C 4/12; C07C 4/14; C07C 4/18
USPC ................................................ 585/484, 485
See application file for complete search history.

(56) References Cited

U.S. PATENT DOCUMENTS

| 2,836,632 | A | 5/1958 | Fetterly |
| 2,881,226 | A | 4/1959 | Wadsworth |
| 2,885,452 | A * | 5/1959 | Schmerling ............... C07C 4/00 585/427 |
| 2,954,413 | A | 9/1960 | Kroeper |
| 3,053,760 | A | 9/1962 | Henke |
| 3,062,903 | A | 11/1962 | Odioso |
| 3,067,128 | A | 12/1962 | Kimberlin, Jr. |

(Continued)

FOREIGN PATENT DOCUMENTS

| EP | 0200654 A1 | 11/1986 |
| FR | 2768724 A1 | 3/1999 |

OTHER PUBLICATIONS

Al-Jarallah, A. M., et al. "Dimerization of Ethyliene to butene-1" Catalysis Today 14.1 (1992): 1-124.

(Continued)

*Primary Examiner* — Thuan D Dang
(74) *Attorney, Agent, or Firm* — Bracewell LLP; Constance G. Rhebergen

(57) ABSTRACT

Embodiments in the present disclosure describe a process for recovery of lighter mono-aromatic compounds from a stream containing alkyl bridged non-condensed alkyl multi-aromatic compounds by conversion to non-condensed alkyl mono-aromatic compounds. The process includes supplying, to a reactor, a hydrocarbon feedstock containing alkyl bridged non-condensed alkyl aromatic compounds and a hydrogen stream. The process further includes allowing the alkyl-bridged non-condensed alkyl multi-aromatic compounds to react with hydrogen in the presence of a suitable catalyst to produce alkyl mono-aromatic compounds. The process may include processing the alkyl mono-aromatic compounds to produce valuable products, such as para-xylene. Various other embodiments are disclosed and claimed.

29 Claims, 4 Drawing Sheets

(56) References Cited

U.S. PATENT DOCUMENTS

| | | | |
|---|---|---|---|
| 3,075,022 | A | 1/1963 | Gammon |
| 3,116,345 | A | 12/1963 | Slaymaker |
| 3,204,007 | A | 8/1965 | Mukai |
| 3,373,217 | A | 3/1968 | Engelbrecht et al. |
| 3,441,625 | A | 4/1969 | Bargeron |
| 3,557,234 | A | 1/1971 | Henry |
| 3,557,235 | A | 1/1971 | Henry |
| 4,192,961 | A | 3/1980 | Gankin |
| 4,242,531 | A | 12/1980 | Carter |
| 4,324,935 | A | 4/1982 | Wernicke |
| 4,484,016 | A | 11/1984 | Maschmeyer |
| 4,532,370 | A | 7/1985 | Le Quan |
| 4,538,018 | A | 8/1985 | Carter |
| 7,723,554 | B2 | 5/2010 | Arca |
| 7,880,045 | B2 | 2/2011 | Arca |
| 7,964,763 | B2 | 6/2011 | Dixon |
| 8,168,844 | B2 | 5/2012 | Arca |
| 2015/0299069 | A1 | 10/2015 | Azam |

OTHER PUBLICATIONS

Buchanan, et al. "Acid-Catalyzed Cracking of Surface-Immobilized 1, 3-Diphenylpropane in Dispersed Solids." Abstracts of Papers of the American Chemical Society. vol. 201. 1155 16th St, NW, Washington, DC 20036: Amer Chemical Soc, 1991. (pp. 536-541).

Farrell, L. M., "Developments in LAO Comonomer Technologies for Polyethylene" PERP 2011S11 Report: May 2012 (pp. 1-7).

Smith, P. D., et al. "Ethylene dimerization over supported titanium alkoxides." Journal of Catalysis 105.1 (1987): 187-198.

Smolin, E. M., et al. "Preparation of Substituted Styrenes by Cracking of Diarylethanes." Industrial & Engineering Chemistry Product Research and Development 3.1 (1964): 16-19.

Wei, Xian-Yong, et al. "FeS2-Catalyzed Hydrocracking of. a.OMEGA.-Diarylalkanes." Bulletin of the Chemical Society of Japan 65.4 (1992): 1114-1119.

International Search Report and Written Opinion dated Apr. 19, 2018 for corresponding PCT/US2018/018471.

* cited by examiner

PROCESS FOR RECOVERY OF LIGHT ALKYL MONO-AROMATIC COMPOUNDS FROM HEAVY ALKYL AROMATIC AND ALKYL-BRIDGED NON-CONDENSED ALKYL AROMATIC COMPOUNDS

FIELD

This disclosure relates to the recovery of light alkylated mono-aromatics from streams containing alkyl-bridged non-condensed alkylated multi-aromatic compounds and heavy alkyl-aromatic compounds during a hydrocarbon refining process.

BACKGROUND

In an aromatics complex, a variety of process units are used to convert naphtha or pyrolysis gasoline into benzene, toluene and mixed xylenes, which are basic petrochemical intermediates used for the production of various other chemical products. In order to maximize the production of benzene, toluene and mixed xylenes, the feed to an aromatics complex is generally limited from $C_6$ up to $C_{11}$ compounds. In most aromatics complexes, the mixed xylenes are processed within the complex to produce the particular isomer—para-xylene, which can be processed downstream to produce terephthalic acid. This terephthalic acid is used to make polyesters, such as polyethylene terephthalate. In order to increase the production of benzene and para-xylene, the toluene and $C_9$ and $C_{10}$ aromatics are processed within the complex through a toluene, $C_9$, $C_{10}$ transalkylation/toluene disproportionation (TA/TDP) process unit to produce benzene and xylenes. Any remaining toluene, $C_9$, and $C_{10}$ aromatics are recycled to extinction. Compounds heavier than $C_{10}$ are generally not processed in the TA/TDP unit, as they tend to cause rapid deactivation of the catalysts used at the higher temperatures used in these units, often greater than 400° C.

When para-xylene is recovered from mixed xylenes by a selective adsorption process unit in the complex, the $C_8$ feed to the selective adsorption unit is processed to eliminate olefins and alkenyl aromatics such as styrene in the feed. Olefinic material can react and occlude the pores of the zeolite adsorbent. The olefinic material is removed by passing a $C_{8+}$ stream across a clay or acidic catalyst to react olefins and alkenyl aromatics with another (typically aromatic) molecule, forming heavier compounds ($C_{16+}$). These heavier compounds are typically removed from the mixed xylenes by fractionation. The heavy compounds cannot be processed in the TA/TDP unit due to their tendency to deactivate the catalyst and are generally removed from the complex as lower value fuels blend stock.

Also during hydrocarbon processing, compounds composed of an aromatic ring with one or more coupled alkyl groups containing three or more carbon molecules per alkyl group may be formed. Formation of these compounds may be from processes used by petroleum refiners and petrochemical producers to produce aromatic compounds from non-aromatic hydrocarbons, such as catalytic reforming. As many of these heavy alkyl aromatic compounds fractionate with the fractions containing greater than 10 carbon atoms, they are not typically sent as feedstock to the transalkylation unit, and instead are sent to gasoline blending or used as fuel oil.

SUMMARY

A need has been recognized for the characterization and recovery of higher value light aromatics in the range from $C_6$ to $C_{10}$ from certain heavy compounds before processing aromatic streams through specialized product production units, such as the TA/TDP unit. Embodiments disclosed here include characterization of the products formed during the treatment of aromatics streams during processing of hydrocarbons. Certain embodiments include processes for recovery of alkyl mono-aromatic compounds. An example of one such process includes the steps of supplying, to a reactor, a feed stream containing one or more of heavy alkyl aromatic compounds and alkyl-bridged non-condensed alkyl multi-aromatic compounds; supplying, to the reactor, a hydrogen stream; allowing the feed stream and the hydrogen stream to react in presence of a catalyst under specific reaction conditions to produce a product stream containing one or more alkyl mono-aromatic compounds; and recovering, from the reactor, the product stream for a downstream process. The downstream process can be a para-xylene recovery process. The alkyl-bridged non-condensed alkyl multi-aromatic compounds include at least two benzene rings connected by an alkyl bridge group having at least two carbons, wherein the benzene rings are connected to different carbons of the alkyl bridge group. In certain embodiments, the feed stream includes $C_{9+}$ alkyl aromatic compounds obtained from a xylene rerun column. The feed stream can be supplied to the reactor without being diluted by a solvent.

In certain embodiments, the hydrogen stream is combined with the feed stream before being supplied to the reactor. In certain embodiments, the hydrogen stream includes a recycled hydrogen stream and a makeup hydrogen stream. In certain embodiments, the hydrogen stream comprises at least 70% hydrogen by weight. The catalyst can be presented as a catalyst bed in the reactor. In certain embodiments, a portion of the hydrogen stream is fed to the catalyst bed in the reactor to quench the catalyst bed. In certain embodiments, the catalyst bed is comprised of two or more catalyst beds. The catalyst can include a support being at least one member of the group consisting of silica, alumina, and combinations thereof, and can further include an acidic component being at least one member of the group consisting of amorphous silica-alumina, zeolite, and combinations thereof. In certain embodiments, the catalyst includes an IUPAC Group 8-10 metal and an IUPAC Group 6 metal. In certain embodiments, the catalyst includes an IUPAC Group 8-10 metal being at least one member of the group consisting of iron, cobalt, and nickel, and combinations thereof and further includes an IUPAC Group 6 metal being at least one member of the group consisting of molybdenum and tungsten, and combinations thereof. In certain embodiments, the IUPAC Group 8-10 metal is 2 to 20 percent by weight of the catalyst and the IUPAC Group 6 metal is 1 to 25 percent by weight of the catalyst. In certain embodiments, the catalyst is comprised of nickel, molybdenum, ultrastable Y-type zeolite, and γ-alumina support.

In certain embodiments, the specific reaction conditions include an operating temperature of the reactor during the hydrodearylation reaction being in the range of 200 to 450° C. The operating temperature of the reactor during the hydrodearylation reaction can be about 300° C. The operating temperature of the reactor during the hydrodearylation reaction can be about 350° C. The specific reaction conditions can include an hydrogen partial pressure of the reactor during the hydrodearylation reaction being in the range of 5 to 50 bar gauge. The hydrogen partial pressure of the reactor during the hydrodearylation reaction can be maintained at less than 20 bar gauge. The specific reaction conditions can include a feed rate of the hydrogen stream being in the range of 500 to 5000 standard cubic feet per barrel of feedstock.

Certain embodiments of the process further includes the step of supplying, to the reactor, a recycled hydrocarbon stream containing unreacted alkyl-bridged non-condensed alkyl multi-aromatic compounds. The recycled hydrocarbon stream can be combined with the feed stream to form a combined feed stream being supplied to the reactor. The hydrogen stream can be combined with the combined feed stream to form a second combined stream being supplied to the reactor. Certain embodiments of the process further includes the step of supplying the product stream to a separation zone to separate the product into a lighter hydrocarbon stream and a heavier hydrocarbon stream. The lighter hydrocarbon stream can be processed to provide a recycled hydrogen stream. The recycled hydrogen stream can be combined with a makeup hydrogen stream to provide the hydrogen stream for supplying to the reactor. Certain embodiments of the process further includes the steps of: supplying the product stream to a first separator to provide a first light stream and a first heavy stream; supplying the first light stream to a second separator to provide a second light stream and a second heavy stream. The first heavy stream and the second heavy stream are combined to form a heavier hydrocarbon stream. Certain embodiments of the process further includes the step of supplying the heavier hydrocarbon stream to a fractionation zone for fractionating into two or more streams. Certain embodiments of the process further includes the step of supplying the heavier hydrocarbon stream to a first fractionator for fractionating into a first light fractionation stream and a first heavy fractionation stream. Then, at least a portion of the first light fractionation stream is fed to a xylene complex for further processing, and the first heavy fractionation stream is supplied to a second fractionator for fractionating into a second light fractionation stream and a second heavy fractionation stream. The second light fractionation stream is supplied to the xylene complex, and at least a portion of the second heavy fractionation stream is recycled to the reactor.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION

Figure 1:
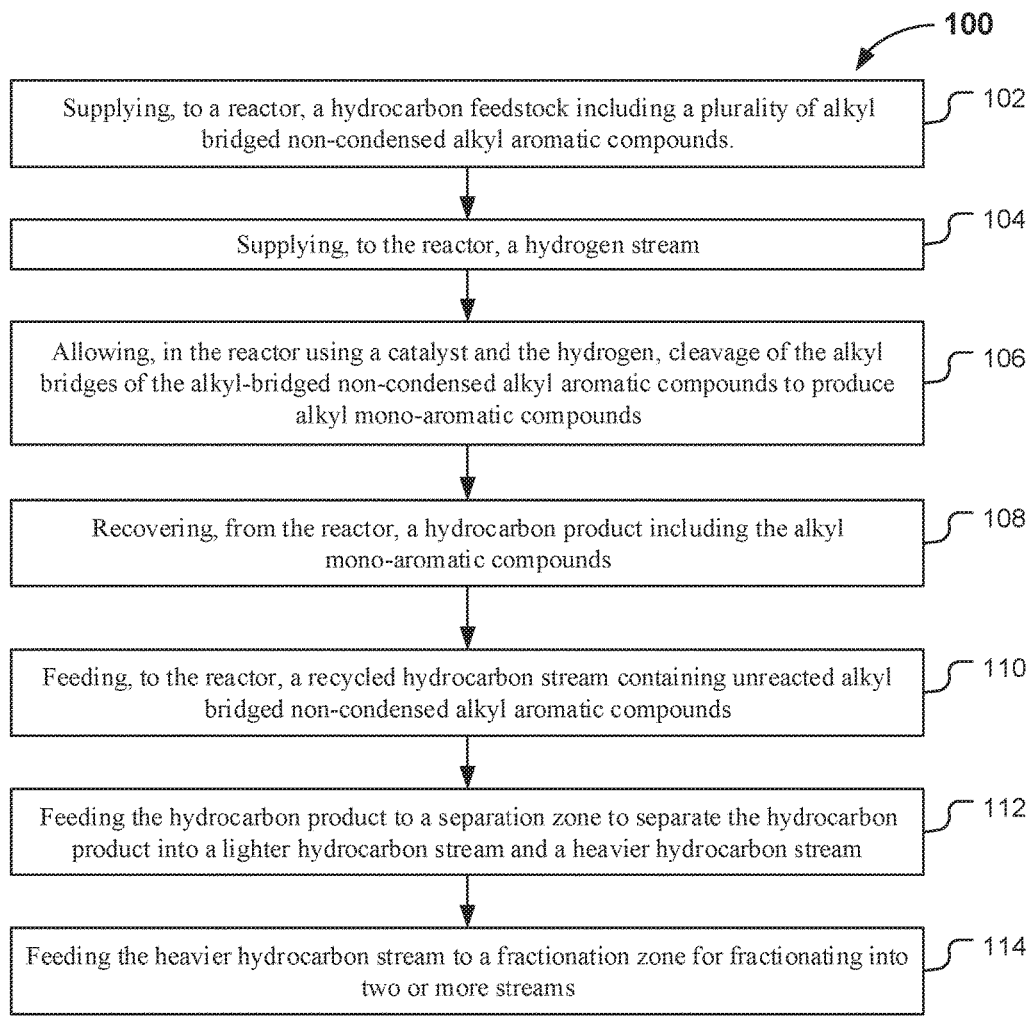
FIG. 1 schematically illustrates a process for the conversion of alkyl-bridged non-condensed alkyl aromatic compounds to non-condensed alkyl aromatic compounds, in accordance with various embodiments.

The present disclosure describes various embodiments related to processes, devices, and systems for conversion of alkyl-bridged non-condensed alkyl aromatic compounds to alkyl mono-aromatic compounds. Further embodiments are described and disclosed.

In the following description, numerous details are set forth in order to provide a thorough understanding of the various embodiments. In other instances, well-known processes, devices, and systems may not been described in particular detail in order not to unnecessarily obscure the various embodiments. Additionally, illustrations of the various embodiments may omit certain features or details in order to not obscure the various embodiments.

In the following detailed description, reference is made to the accompanying drawings that form a part of this disclosure. The drawings may provide an illustration of some of the various embodiments in which the subject matter of the present disclosure may be practiced. Other embodiments may be utilized, and logical changes may be made without departing from the scope of this disclosure. Therefore, the following detailed description is not to be taken in a limiting sense.

The description may use the phrases "in some embodiments," "in various embodiments," "in an embodiment," or "in embodiments," which may each refer to one or more of the same or different embodiments. Furthermore, the terms "comprising," "including," "having," and the like, as used with respect to embodiments of the present disclosure, are synonymous.

As used in this disclosure, the term "hydrodearylation" refers to a process for the cleaving of the alkyl bridge of non-condensed alkyl-bridged multi-aromatics or heavy alkyl aromatic compounds to form alkyl mono-aromatics, in the presence a catalyst and hydrogen.

As used in this disclosure, the term "stream" (and variations of this term, such as hydrocarbon stream, feed stream, product stream, and the like) may include one or more of various hydrocarbon compounds, such as straight chain, branched or cyclical alkanes, alkenes, alkadienes, alkynes, alkyl aromatics, alkenyl aromatics, condensed and non-condensed di-, tri- and tetra-aromatics, and gases such as hydrogen and methane, $C_{2+}$ hydrocarbons and further may include various impurities.

As used in this disclosure, the term "zone" refers to an area including one or more equipment, or one or more sub-zones. Equipment may include one or more reactors or reactor vessels, heaters, heat exchangers, pipes, pumps, compressors, and controllers. Additionally, an equipment, such as reactor, dryer, or vessels, further may include one or more zones.

As used in this disclosure, the term "rich" means an amount of at least 50% or greater, by mole percentage of a compound or class of compounds in a stream. Certain streams rich in a compound or class of compounds can contain about 70% or greater, by mole percentage of the particular compound or class of compounds in the streams. In certain cases, mole percentage may be replaced by weight percentage, in accordance with standard industry usage.

As used in this disclosure, the term "substantially" means an amount of at least 80%, by mole percentage of a compound or class of compounds in a stream. Certain streams substantially containing a compound or class of compounds can contain at least 90%, by mole percentage of the compound or class of compounds in the streams. Certain streams substantially containing a compound or class of compounds can contain at least 99%, by mole percentage of the compound or class of compounds in the streams. In certain cases, mole percentage may be replaced by weight percentage, in accordance with standard industry usage.

As used in this disclosure, the term "mixed xylenes" refers to a mixture containing one or more $C_8$ aromatics, including any one of the three isomers of di-methylbenzene and ethylbenzene.

As used in this disclosure, the term "conversion" refers to the conversion of compounds containing multiple aromatic rings or mono-aromatic compounds with heavy ($C_{4+}$) alkyl groups boiling above 210° C. to mono-aromatic compounds with a lighter alkyl groups boiling below 210° C.

The oligomer byproducts formed by the reaction of olefinic hydrocarbons across an acid catalyst are heavy aromatics and must be removed by fractionation. The nature of the byproducts formed has not been well characterized. Embodiments of the disclosure here include characterization of the $C_{8+}$ fraction of reformate. In certain embodiments, the $C_{8+}$ fraction of reformate primarily contains aromatics (generally more than 95%). The olefinic species in this fraction are composed primarily of alkenyl aromatics, such as styrene and methyl-styrene. Such molecules would be expected to react across clay-containing Lewis-acid sites at temperatures around 200° C. with the alkyl aromatics via a Friedel-Crafts reaction to form molecules with two aromatic rings connected with an alkyl bridge. Alkenyl aromatics may react, in turn, with these compounds to form multi-aromatic compounds with three or more aromatic rings connected by alkyl bridges. Such multi-aromatic compounds may be characterized as having a relatively high density (greater than 900 kg/m3), a darker brown color (Standard Reference Method Color greater than 20), and higher boiling points (greater than 280° C.), as compared to non-bridged alkyl aromatics. The remaining non-aromatic olefin portion of the $C_{8+}$ fraction of reformate in this embodiment would be expected to react across clay-containing Lewis acid sites, at temperatures around 200° C., with alkyl aromatics via a Friedel-Crafts reaction to form mono-aromatic molecules with at least one large (more than 7 carbon atoms) alkyl group. Such heavy mono-aromatics may be characterized as having a moderately high density (greater than 800 kg/m3), and higher boiling points (greater than 250° C.), as compared to lighter alkyl aromatics. Such heavy molecules are separated from $C_9$ and $C_{10}$ mono-aromatics by fractionation before the $C_9$ and $C_{10}$ aromatics are sent to the TA/TDP process unit for conversion to benzene and xylenes.

Processing of a stream containing multi-aromatic compounds may include separation from lighter unreacted alkyl aromatics by fractionation, where a separation process may provide at least one low-boiling point (or light) fraction containing reduced levels of olefins and at least one high-boiling point (or heavy) fraction containing the multi-aromatic compounds along with high boiling point alkyl aromatics. The heavy fraction containing the multi-aromatic compounds may be utilized as a stream for gasoline blending because it has a relatively high octane; however, the high density, darker brown color, and high final boiling point may limit the amount that may be blended into a gasoline stream. Alternatively, the heavy fraction containing the multi-aromatic compounds may be utilized as a fuel oil blend component. The heavy fraction containing the multi-aromatics typically is not processed in catalytic units such as a toluene/$C_9$/$C_{10}$ transalkylation unit, because the condensed multi-aromatics in the heaviest fractions with greater than ten carbon atoms tend to form catalyst-deactivating coke layers at the conditions used in such units. The formation of coke layers potentially limits catalyst life between regenerations. Accordingly, alternative processing methods and systems are needed to optimize the use of a hydrocarbon process stream containing alkyl-bridged non-condensed alkyl aromatic compounds.

Certain embodiments disclosed here relate to recovery of light alkylated mono-aromatics from streams containing alkyl-bridged non-condensed alkylated multi-aromatic compounds and heavy alkyl-aromatic compounds during a hydrocarbon refining process. Alkyl-bridged non-condensed alkyl aromatic compounds may be referred to as multi-aromatics or poly-aromatics. Conversion of multi-aromatics into alkyl mono-aromatics may be desirable to optimize the use of hydrocarbon process streams containing multi-aromatics. In various embodiments, recovery processes provide alkyl mono-aromatic compounds that have retained the high octane properties of the multi-aromatics. Retaining a high octane may be desirable for gasoline blending of the alkyl aromatics. In various embodiments, the density, color, and boiling point properties may be improved by the recovery processes, resulting in a higher value hydrocarbon stream for blending into gasoline streams. In various embodiments, the processes for conversion of multi-aromatics into alkyl aromatics may allow for the use of the alkyl aromatics as feedstock to a benzene, toluene, ethylbenzene, and xylenes (BTEX) petrochemicals processing unit. In various embodiments, the processes for conversion of multi-aromatics into alkyl aromatics may allow for the use of the alkyl aromatics as feedstock within a TA/TDP unit. Accordingly, certain embodiments may provide higher value use of a hydrocarbon stream containing multi-aromatics by converting these compounds to alkyl aromatics.

Certain embodiments disclosed here relate to methods for recovery of light alkylated mono-aromatics from streams containing alkyl-bridged non-condensed alkylated multi-aromatic compounds and heavy alkyl-aromatic compounds. One such method includes the steps of supplying to a reactor a feed stream containing a plurality of alkyl bridged non-condensed alkyl aromatic compounds and heavy alkyl aromatic compounds; supplying a hydrogen stream to the reactor; allowing the feed stream and the hydrogen stream to react in the presence of a catalyst to produce a product stream containing alkyl mono-aromatic compounds; and recovering, from the reactor, the product stream. The alkyl-bridged non-condensed alkyl aromatic compounds include at least two benzene rings connected by an alkyl bridge group having at least two carbons, wherein the benzene rings are connected to at least two different carbons of the alkyl bridge group. The feed stream can be a $C_{9+}$ heavy aromatics stream from a xylenes rerun column. The feed stream can be a $C_{9+}$ aromatics stream, which includes di, tri, and poly aromatics ($C_9$ to $C_{16+}$). In certain embodiments, the feed stream may be diluted by a solvent or may be supplied without any dilution by a solvent. In certain embodiments, the feed stream is combined with the hydrogen stream and supplied as a combined stream to the reactor. In certain embodiments, the hydrogen stream includes a combination of a recycled hydrogen stream and a makeup hydrogen stream. The hydrogen stream can contain at least 70% hydrogen by weight. The catalyst may be provided as a catalyst bed in the reactor. In certain embodiments, a portion of the hydrogen stream is fed to the catalyst bed of the reactor to quench the catalyst bed. The catalyst bed may include two or more catalyst beds. In certain embodiments, the catalyst includes a support selected from the group consisting of silica and alumina, and combinations thereof, and further includes an acidic component selected from the group consisting of amorphous silica-alumina and zeolite, and combinations thereof. The catalyst can include an IUPAC Group 8-10 metal and an IUPAC Group 6 metal. The catalyst can include an IUPAC Group 8-10 metal selected from the group consisting of iron, cobalt, and nickel, and combinations thereof, and further includes an IUPAC Group 6 metal selected from the group consisting of molybdenum and tungsten, and combinations thereof. Certain catalysts used here contain the IUPAC Group 8-10 metal as 2 to 20 percent by weight of the catalyst and the IUPAC Group 6 metal as 1 to 25 percent by weight of the catalyst. The catalyst can include one or more of nickel, molybdenum, ultrastable Y-type zeolite, and γ-alumina support. The reactor is operated under suitable temperature and pressure conditions for optimal recovery of the alkylated monoaromatics. Such operating conditions can include maintaining the temperature of the reactor between 200 to 450° C. during the hydrodearylation reaction. Such operating conditions can include maintaining the temperature of the reactor around 300° C. to 350° C. during the hydrodearylation reaction. The hydrogen partial pressure of the reactor can range from 5 to 50 bar gauge. The hydrogen partial pressure of the reactor can be maintained at less than 20 bar gauge. The feed rate of the hydrogen stream can be 500 to 5000 standard cubic feet per barrel of the hydrocarbon feed stream. Operating conditions can include a liquid hourly space velocity of the reactor of about 0.5 to 10 per hour.

Certain embodiments of the method can also include the step of supplying, to the reactor, a recycled hydrocarbon stream including a plurality of unreacted alkyl bridged non-condensed alkyl aromatic compounds. In certain embodiments, the recycled hydrocarbon stream is combined with the feed stream and supplied to the reactor as a single stream. In certain embodiments, the hydrogen stream can be combined with the combined feed stream of the recycled hydrocarbon stream and the feed stream and supplied to the reactor as a single stream. Certain embodiments can include supplying the product stream to a separation zone to separate the product into a lighter hydrocarbon stream and a heavier hydrocarbon stream. In certain embodiments, the product stream includes $C_8$ to $C_{10}$ range alkyl mono-aromatics. In certain embodiments, the majority of the olefins obtained from the heavy reformate clay treaters (C8+) are primarily alkenyl aromatics, and they will react with alkyl aromatics to form the uncondensed alkyl multi-aromatics. The uncondensed alkyl multi-aromatics are hydrodearylated at relatively low temperature and pressure in these certain embodiments, allowing for the conversion to alkyl mono-aromatics while avoiding the excessive catalyst deactivation expected at higher temperatures with a heavy stream. Certain embodiments can include supplying the product stream to a paraxylene recovery process.

FIG. 1 schematically illustrates a process 100 for the recovery of light alkylated mono-aromatics from streams containing alkyl-bridged non-condensed alkylated multi-aromatic compounds and heavy alkyl-aromatic compounds, in accordance with various embodiments. The step 102 of process 100 includes supplying, to a reactor, a hydrocarbon feedstock including a plurality of alkyl bridged non-condensed alkyl multi-aromatic compounds. In various embodiments, the alkyl bridged non-condensed alkyl aromatic compounds include at least two benzene rings connected by an alkyl bridge group having at least two carbons, where the benzene rings are connected to different carbons of the alkyl bridge group. In various embodiments, the alkyl bridged non-condensed alkyl aromatic compounds include additional alkyl groups connected to the benzene rings of the alkyl bridged non-condensed alkyl aromatic compounds. The hydrocarbon feedstock can be a stream in a petroleum refinery from one or more hydrocarbons treatments. In various embodiments, the hydrocarbon feedstock may comprise a heavy aromatics stream from a unit operation of a petroleum refinery. In various embodiments, the hydrocarbon feedstock may comprise a $C_{9+}$ heavy aromatics stream from a xylene rerun column of a petroleum refinery. In various embodiments, the hydrocarbon feedstock is undiluted by a solvent.

By way of example and not limitation, the various alkyl bridged non-condensed alkyl aromatic compounds may include a mixture of chemical compounds illustrated by Formula I, Formula II, and Formula III, and various combinations of these compounds.

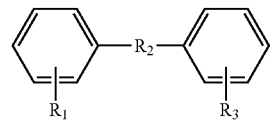

[Formula I]

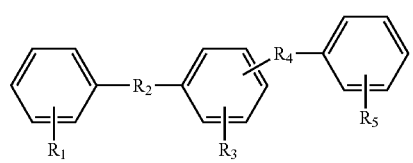

[Formula II]

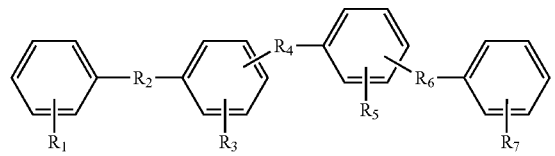

[Formula III]

$R_2$, $R_4$, and $R_6$ are alkyl bridge groups independently having from two to six carbon atoms. $R_1$, $R_3$, $R_5$, and $R_7$ are independently selected from the group consisting of hydrogen and an alkyl group having from one to eight carbon atoms. In addition to the groups $R_1$, $R_3$, $R_5$, and $R_7$, the benzene groups of Formulas I, II, and III may further include additional alkyl groups connected to the benzene groups, respectively. In addition to the four benzene groups of Formula III, the various alkyl bridged non-condensed alkyl aromatic compounds may include five or more benzene groups connected by alkyl bridges, where the additional benzene groups further may include alkyl groups connected to the additional benzene groups.

The step 104 of process 100 includes supplying, to the reactor, a hydrogen stream. In various embodiments, the hydrogen stream may be combined with the hydrocarbon feedstock to form a combined feedstock stream that is subsequently fed to the reactor. In various embodiments, the hydrogen stream may include a recycled hydrogen stream and a makeup hydrogen stream. In various embodiments, the recycled hydrogen stream may be a stream from processing of a hydrocarbon product stream from the reactor. In various embodiments, the hydrogen stream may contain at least 70 mole percent hydrogen. In various embodiments, the hydrogen stream may contain at least 80 mole percent hydrogen. In various embodiments, the hydrogen stream may contain at least 90 mole percent hydrogen.

The step 106 of process 100 includes allowing a hydrodearylation reaction to occur in the presence of a catalyst under suitable reaction conditions, such that the alkyl bridges of the alkyl bridged non-condensed alkyl multi-aromatic compounds and heavy alkyl aromatic compounds are cleaved to produce alkyl mono-aromatic compounds. In various embodiments, non-bridging alkyl groups connected to the benzene rings of the alkyl bridged non-condensed alkyl aromatic compounds remain connected to the benzene rings of the non-condensed alkyl aromatic compounds in the hydrocarbon product. By way of example and not limitation, the various alkyl mono-aromatic compounds may include a mixture of chemical compounds illustrated by Formula IV.

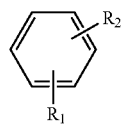

[Formula IV]

For the various alkyl mono-aromatic compounds, $R_1$ is independently selected from the group consisting of an alkyl group having from one to eight carbon atoms, and $R_2$ is independently selected from the group consisting of hydrogen and an alkyl group having from one to eight carbon atoms.

In various embodiments, an operating temperature of the reactor may be 200 to 450° C., within reasonable engineering tolerances, during the cleaving of the alkyl bridges. In various embodiments, the operating temperature for the reactor may be approximately 300° C., within reasonable engineering tolerances, for the cleaving of the alkyl bridges. In various embodiments, the operating temperature for the reactor may be 350° C., within reasonable engineering tolerances, for the cleaving of the alkyl bridges. In various embodiments, an hydrogen partial pressure of the reactor may be 5 to 50 bar gauge, within reasonable engineering tolerances. In various embodiments, the hydrogen partial pressure for the reactor may be less than 20 bar gauge, within reasonable engineering tolerances. In various embodiments, a feed rate of the hydrogen stream may be 500 to 5000 standard cubic feet per barrel of feedstock, within reasonable engineering tolerances. In various embodiments, a liquid hourly space velocity of the reactor may be 0.5 to 10 per hour, within reasonable engineering tolerances.

The step 108 of process 100 includes recovering, from the reactor, a hydrocarbon product containing the alkyl mono-aromatic compounds. In various embodiments, the hydrocarbon product may be an effluent stream from the reactor. In various embodiments, the effluent stream may be fed to various separation processes to recover unreacted hydrogen, the alkyl mono-aromatic compounds, and the unreacted alkyl-bridged non-condensed alkyl aromatic compounds. In various embodiments, the recovered unreacted hydrogen may be recycled back to the reactor. In various embodiments, the unreacted alkyl-bridged non-condensed alkyl aromatic compounds may be partially recycled back to the reactor. In various embodiments, the alkyl mono-aromatic compounds may be further processed to recovery various high value hydrocarbons.

The step 110 of process 100 includes supplying, to the reactor, a recycled hydrocarbon stream including a plurality of unreacted alkyl bridged non-condensed alkyl aromatic compounds. In various embodiments, the recycled hydrocarbon stream may be a stream from processing of a hydrocarbon product from the reactor. In various embodiments, the recycled hydrocarbon stream may be combined with the feedstock stream to form a combined feedstock stream that is fed to the reactor. In various embodiments, the hydrogen stream may be combined with the combined feed stream to form a second combined stream that is fed to the reactor. In various embodiments, the recycled hydrocarbon stream, the hydrogen stream, and the feedstock stream may be combined in any order to form a combined stream that is fed to the reactor. In various embodiments, the recycled hydrocarbon stream, the hydrogen stream, and the feedstock stream may be fed separately to the reactor or two of the streams may be combined and the other fed separately to the reactor. In various embodiments, the hydrogen stream has a portion of the stream fed directly to one or more catalyst beds of the reactor.

The step 112 of process 100 includes supplying, the hydrocarbon product to a separation zone to separate the hydrocarbon product into a lighter hydrocarbon stream and a heavier hydrocarbon stream. In various embodiments, the separation zone may comprise a first separator and a second separator. The hydrocarbon product may be fed to the first separator to provide a first light stream and a first heavy stream from the first separator. The first light stream may be fed to the second separator to provide a second light stream and a second heavy stream. The first heavy stream and the second heavy stream may be combined to form the heavier hydrocarbon stream. The second light stream may be the lighter hydrocarbon stream from the separation zone. In various embodiments, the lighter hydrocarbon stream may be processed to provide a recycled hydrogen stream. In various embodiments, the recycled hydrogen stream may be combined with a makeup hydrogen stream to provide the hydrogen stream to be supplied to the reactor.

The step 114 of process 100 includes supplying the heavier hydrocarbon stream to a fractionation zone for fractionating into two or more streams. In various embodiments, the fractionation zone may comprise a first fractionator and a second fractionator. The heavier hydrocarbon stream may be fed to the first fractionator for fractionating into a first light fractionation stream and a first heavy fractionation stream. At least a portion of the first light fractionation stream may be fed to a xylene complex for processing to recover xylenes. The first heavy fractionation stream may be fed to the second fractionator for fractionating into a second light fractionation stream and a second heavy fractionation stream. The second light fractionation stream may be fed to the xylene complex for recovery of xylenes. In various embodiments, a portion of the second heavy fractionation stream may be recycled to the reactor to provide the recycled hydrocarbon stream. In various embodiments, a portion of the second heavy fractionation stream may be a bleed stream to prevent buildup of the alkyl-bridged non-condensed alkyl aromatic compounds in the various process flow streams. A flow rate of the bleed stream may be adjusted accordingly to ensure no heavy aromatic hydrocarbon build up in the various process flow streams.

Figure 2:
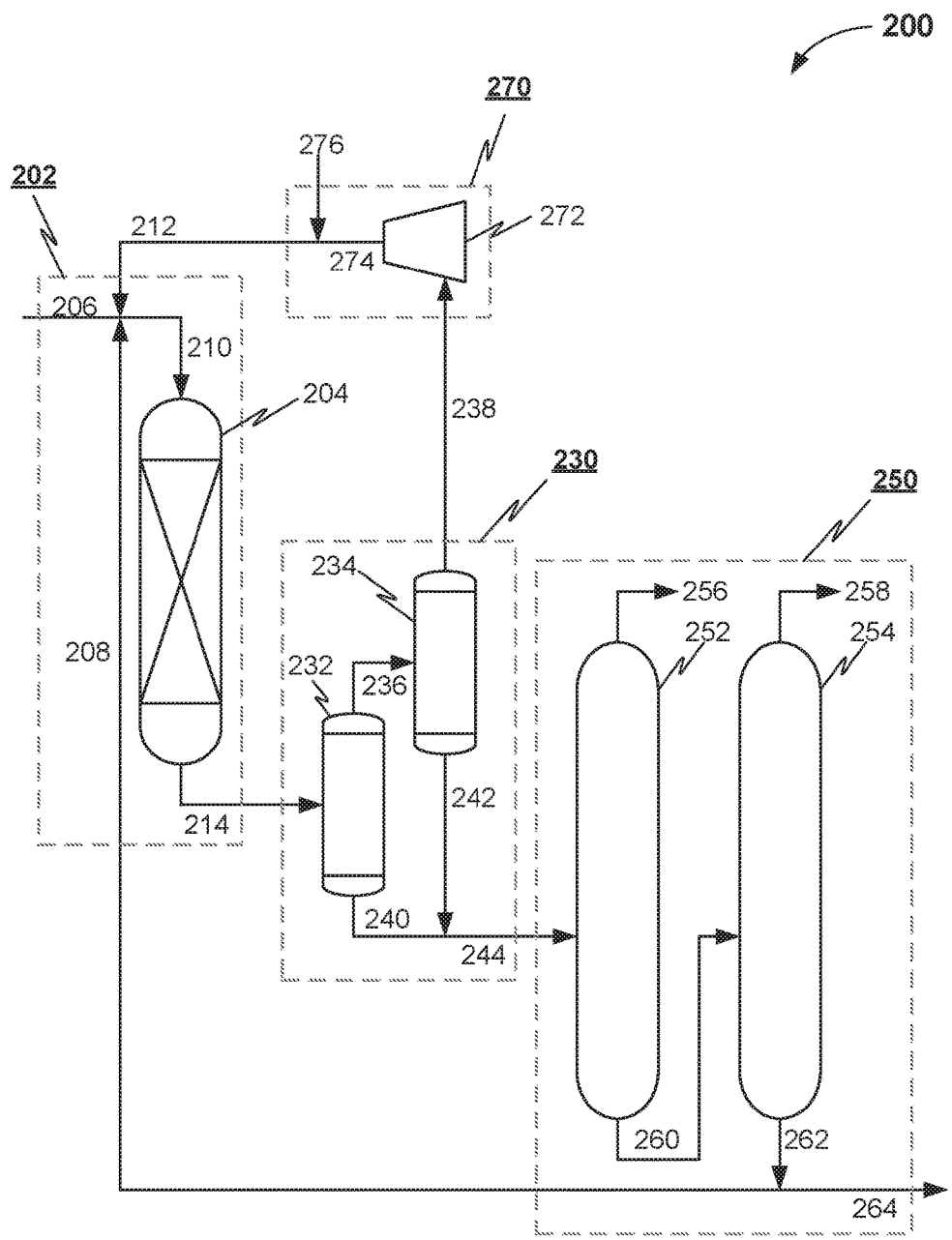
FIG. 2 schematically illustrates a system for the conversion of alkyl-bridged non-condensed alkyl aromatic compounds to non-condensed alkyl aromatic compounds, in accordance with various embodiments.

FIG. 2 schematically illustrates a system 200 for the conversion of alkyl-bridged non-condensed alkyl aromatic compounds to alkyl mono-aromatic compounds, in accordance with various embodiments. The system 200 may be referred to as a single stage hydrodearylation system for the conversion of heavy aromatics to non-condensed alkyl aromatics. The various process flow lines illustrated in FIG. 2 may be referred to as streams, feeds, products, or effluents. Additionally, not all heat transfer, mass transfer, and fluid conveying equipment are illustrated, and the requirements for these items are well understood by a person of ordinary skill in the art.

The system 200 may include a hydrodearylation reaction zone 202. The reaction zone 202 may include a reactor 204. The reactor 204 may include an effective quantity of a suitable catalyst. The catalyst may be in a catalyst bed. The reactor 204 may include an inlet for receiving a combined stream 210 including a feedstock stream 206, a recycle stream 208, and a hydrogen stream 212. The feedstock stream 206 may be a stream including $C_{9+}$ aromatics. A hydrodearylated effluent stream 214 may be discharged from an outlet of reactor 204. The hydrodearylation reactor 204 may have a single or multiple catalyst beds and may receive quench hydrogen stream in between the beds of a multi-bed arrangement. Although not shown, the quench hydrogen stream may be a portion of the hydrogen stream 212 piped to the various locations of the catalyst beds in the reactor 204.

In various embodiments, the degree of conversion in the hydrodearylation zone 202 may be kept below a threshold to limit the amount of catalyst required and the amount of coking on the catalyst. By way of example and not limitation, a threshold limit may be 70% of a maximum potential conversion in the reactor 204. The hydrodearylated effluent stream 214 may pass to a separation zone 230. The separation zone may include two separators, a hot separator 232 and the cold separator 234. The hot separator 232 may include an inlet for receiving the reactor effluent 214, an outlet for discharging a hydrodearylated gas stream 236, and an outlet for discharging a hydrodearylated liquid stream 240. The cold separator 234 may include an inlet for partially condensed hydrodearylated gas stream 236, an outlet for discharging a vapor stream 238 and outlet for discharging a hydrocarbon liquid stream 242. Heat exchangers may be included to cool the hot stream 236 before entering subsequent cold separator 234. The heat exchangers are not shown and any design requirements for the heat exchangers are well understood by a person having ordinary skill in the art. The stream 236 may include one or more gases selected from a group consisting of hydrogen, methane, ethane, $C_{3+}$ hydrocarbons, and combinations thereof. The stream 236 may exit the hot separator 232 and be fed to the cold separator 234.

The vapor stream 238 from cold separator 234 may be rich in hydrogen. The vapor stream 238 may be recycled back after compression through recycling system 270 with a compressor 272 to produce a stream 274. The stream 274 may be combined with a hydrogen make up stream 276. The hydrogen makeup stream 276 may be a high purity make up gas containing substantially hydrogen from a header. The combined stream may be recycled back to the feed section through the header to provide the hydrogen stream 212.

The liquid stream 242 from the cold separator 234 may be preheated in a heat exchanger train (not shown). The liquid stream 242 may be combined with the hot hydrocarbon liquid stream 240 to form a liquid stream 244, which may flow to a fractionation zone 250.

The fractionation zone 250 may include a stripper column 252 and a splitter column 254. The columns 252, 254 may be reboiled fractionation columns. The liquid stream 244 may enter the stripper column 252. The stripper column 252 may be a trayed column or a packed column, or a combination of the two types of columns. The stripper column 252 may form two streams, a light vapor stream 256 and a bottom stream 260. The vapor stream 256 may be condensed, and a portion may be a liquid reflux for the stripper column 252. A portion of the condensed and non-condensed vapor stream 256 may be routed for further processing. By way of example and not limitation, the condensed and non-condensed vapor stream 256 may be processed in a reformate splitter column or a heavy aromatics column within a para-xylene aromatic complex. These details of further processing are not shown in FIG. 2 as they are understood by a person of ordinary skill in the art.

The bottom stream 260 from stripper column 252 may be routed into the splitter column 254. The splitter column 254 may be a trayed column or a packed column, or a combination of the two types of columns. The splitter column 254 may form two streams, a light stream 258 and a heavy stream 262. The light stream 258 may be comprised of $C_{6+}$ compounds. The heavy stream 262 may be comprised of $C_{10+}$ compounds.

The light stream 258 may be condensed and portion of the condensed light stream may be a liquid refluxed to the splitter column 254. A portion of the light stream 258 that is not refluxed to the splitter column 254 may be routed for further processing. By way of example, this portion of the light stream 258 may be routed to a reforming/para-xylene complex for xylene recovery. The heavy stream 262 may be split into two streams, a recycle stream 208 and a bleed stream 264. A flow rate of the bleed stream 264 may be adjusted accordingly to ensure no heavy aromatic hydrocarbon build up in the reaction stream 210.

In various embodiments, the hydrogen stream 212 may be a once-through stream without recycling via streams 238, 274. Accordingly, a hydrogen stream 276 may be added via a manifold to form hydrogen stream 212 without stream 274. In various embodiments, flashed gases from the cold separator 234 may be routed out of the system 200 and back to a hydrogen generation source (not shown). In various embodiments, when the hydrogen stream 212 is a once-through stream, the separator effluent liquid 244 may be directly routed to a xylene rerun column within a para-xylene complex.

In various embodiments, the hydrodearylation reaction zone 202 may include two reactors in parallel and may be used with an in-situ regeneration loop. As a fixed bed catalyst system is susceptible to coking when processing heavy aromatics, one reactor may be operating while the other reactor is in a regeneration mode for various embodiments.

In various embodiments, the hot and cold separators 232, 234 may be replaced by a single separator with a heat exchanger train to preheat the hydrogen stream 212 or the combined stream 210 with reactor effluent 214.

In various embodiments, the feedstock stream 206 may be a heavy hydrocarbons stream. The heavy hydrocarbons stream may be $C_{9+}$ or $C_{10+}$ from a xylene rerun column or a heavy aromatic column bottoms from a para-xylene aromatic complex. The feedstock stream 206 may include $C_9$ to $C_{16+}$, and this stream may be predominantly mono-aromatics, di-aromatics, and poly-aromatics.

In various embodiments, the hydrodearylation reaction zone 202 may include a reactor 204 having a single catalyst bed or multiple catalyst beds. In various embodiments, the multiple catalyst beds may receive quench a hydrogen stream between the beds. Although not illustrated in FIG. 2, the hydrogen stream 212 may be provided anywhere along the reactor 204, and multiple hydrogen streams may be provided, depending upon the number of beds.

In various embodiments, the reactor 204 may contain a catalyst having at least one IUPAC Group 8-10 metal, and at least one IUPAC Group 6 metal. The IUPAC Group 8-10 metal may be selected from the group consisting of iron, cobalt, and nickel, and combinations thereof. The IUPAC Group 6 metal may be selected from a group consisting of molybdenum and tungsten, and combinations thereof. The IUPAC Group 8-10 metal may be present in an amount of approximately 2-20% by weight, and the IUPAC Group 6 metal may be present in an amount of approximately 1-25% by weight. In various embodiments, the IUPAC Group 8-10 and IUPAC Group 6 metals may be on a support material. In various embodiments, the support material may be silica or alumina, and may further include an acidic component selected from the group consisting of an amorphous silica alumina, a zeolite or a combination of the two. In various embodiments, the reactor 204 may contain a catalyst having any noble IUPAC Group 8-10 metal on a silica-alumina or alumina support having an acid cracking component of an amorphous silica-alumina or a zeolite, or a combination of the two. In certain embodiments, the reactor 204 may contain a catalyst selected from the group consisting of platinum, palladium, and combinations thereof, on a silica-alumina or alumina support having an acid cracking component of an amorphous silica-alumina or a zeolite, or a combination of the two.

In various embodiments, operating conditions for the hydrodearylation reaction zone 202 may include a reaction temperature in the range of from 200° C. to 450° C. (392° F. to 840° F.), and a hydrogen partial pressure in the range of from 5 bar gauge to 50 bar gauge (70 psig to 725 psig). In various embodiments, operating conditions for the hot separator 232 may include a temperature in the range of from 200° C. to 400° C. (392° F. to 750° F.), and a hydrogen partialpressure in the range of from 5 bar gauge to 50 bar gauge (70 psig to 725 psig). In various embodiments, operating conditions for the cold separator 234 may include a temperature in the range of from 40° C. to 80° C. (104° F. to 176° F.), and a pressure in the range of from 5 bar gauge to 50 bar gauge (70 psig to 725 psig). In various embodiments, operating conditions for the fractionation zone 250 may include a temperature in the range of from 40° C. to 300° C. (104° F. to 572° F.), and a pressure in the range of from 0.05 bar to 30 bar (0.73 psig to 435 psig).

Examples

According to various embodiments, the present disclosure describes methods and systems for a hydrodearylation, as illustrated and described for the various embodiments. In an example of a hydrodearylation process, a feedstock consisting of a xylenes rerun column bottoms stream with an ASTM D1500 color of 5, a density of 0.9125 g/cm$^3$, and a 57 weight percent of hydrocarbons boiling below 180° C. (356° F.) was reacted in a hydrodearylation reaction zone containing a catalyst having nickel and molybdenum with ultrastable Y-type (USY) zeolite on a silica-alumina support operated at hydrodearylation conditions including a temperatures from 200 to 450° C. (392 to 842° F.), at a hydrogen partial pressure of 15 bara (218 psia), a liquid hourly space velocity of 1.3 hr$^{-1}$. The results of the hydrodearylation reactions are summarized in FIGS. 3 and 4.

Figure 3:
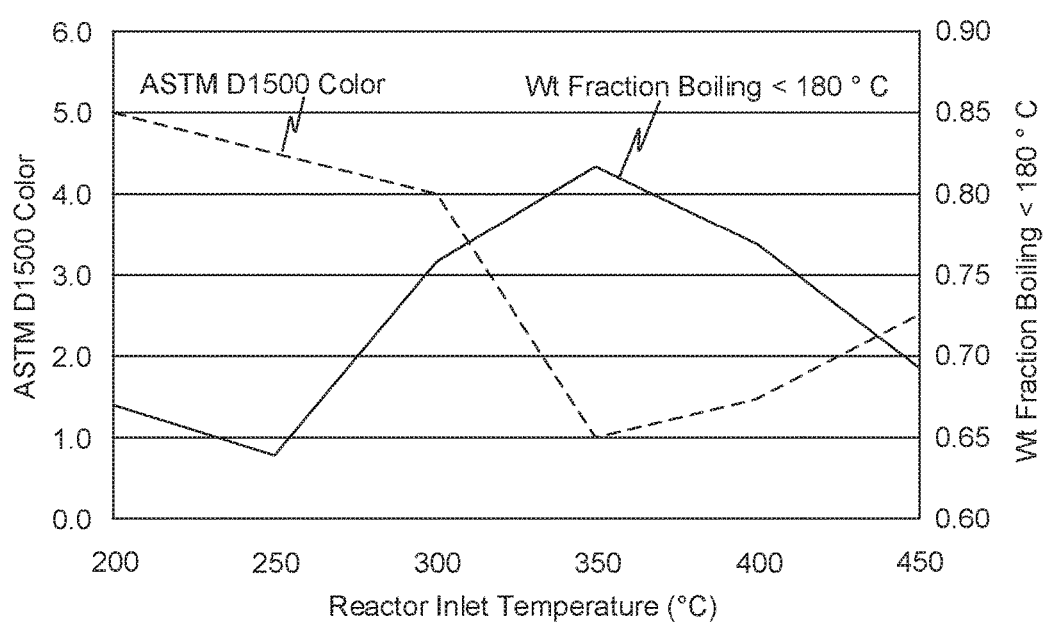
FIG. 3 is a plot of reactor effluent ASTM D1500 color and weight fraction boiling at less than 180° C. as a function of reactor inlet temperature, under reaction conditions described in Examples.
Figure 4:
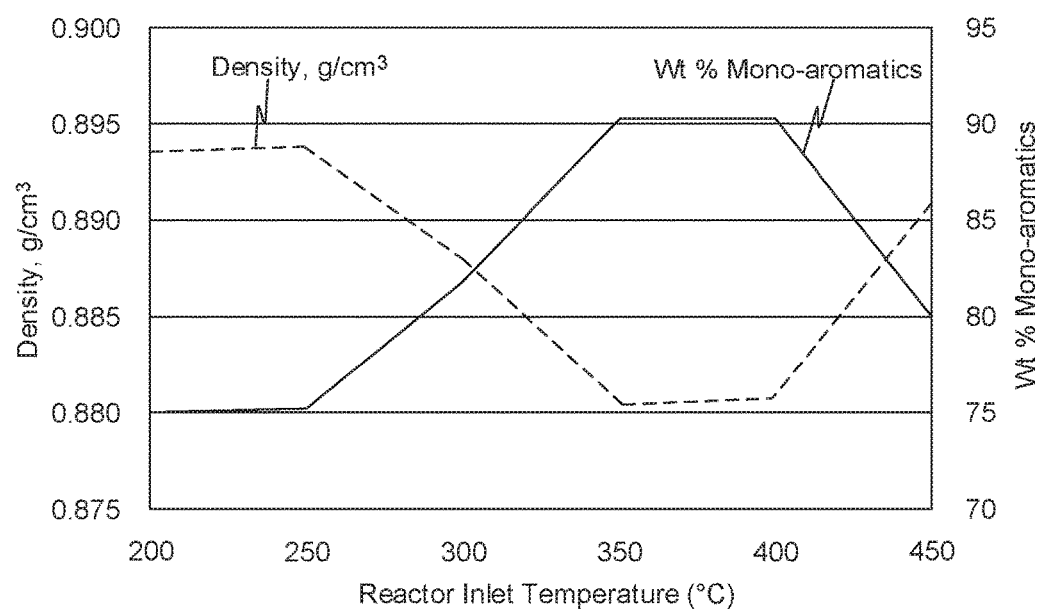
FIG. 4 is a plot of reactor effluent density and weight percentage of mono-aromatics as a function of reactor inlet temperature, under reaction conditions described in Examples.

FIG. 3 is a plot of reactor effluent ASTM D1500 color and weight fraction boiling at less than 180° C. as a function of reactor inlet temperature. As can be seen in FIG. 3, a temperature of approximately 350° C. appears to provide a higher percentage of lower boiling fraction and a lower color value as compared to other inlet reactor temperatures. FIG. 4 is a plot of reactor effluent density and weight percentage of mono-aromatics as a function of reactor inlet temperature. As can be seen in FIG. 4, a reactor inlet temperature between 350° C. and 400° C. appears to provide a higher percentage of mono-aromatics under these reaction conditions and a lower density as compared to other inlet reactor temperatures.

Ranges may be expressed herein as from about one particular value and to about another particular value. When such a range is expressed, it is to be understood that another embodiment is from the one particular value and/or to the other particular value, along with all combinations within said range. Where the range of values is described or referenced herein, the interval encompasses each intervening value between the upper limit and the lower limit as well as the upper limit and the lower limit and includes smaller ranges of the interval subject to any specific exclusion provided.

Where a method comprising two or more defined steps is recited or referenced herein, the defined steps can be carried out in any order or simultaneously except where the context excludes that possibility.

While various embodiments have been described in detail for the purpose of illustration, they are not to be construed as limiting, but are intended to cover all the changes and modifications within the spirit and scope thereof.

What is claimed is:

1. A process for recovery of alkyl mono-aromatic compounds, the process comprising the steps of:
supplying, to a reactor, a feed stream containing one or more of heavy alkyl aromatic compounds and alkyl-bridged non-condensed alkyl multi-aromatic compounds;
supplying, to the reactor, a hydrogen stream;
allowing the feed stream and the hydrogen stream to react in presence of a catalyst under specific reaction conditions to produce a product stream containing one or more alkyl mono-aromatic compounds; and
recovering, from the reactor, the product stream for a downstream process,
wherein the alkyl-bridged non-condensed alkyl multi-aromatic compounds include at least two benzene rings connected by an alkyl bridge group having at least two carbons, wherein the benzene rings are connected to different carbons of the alkyl bridge group.

2. The process of claim 1, wherein the feed stream comprises C$_{9+}$ alkyl aromatic compounds obtained from a xylene rerun column.

3. The process of claim 1, wherein the feed stream is undiluted by a solvent.

4. The process of claim 1, wherein the hydrogen stream is combined with the feed stream before being supplied to the reactor.

5. The process of claim 1, wherein the hydrogen stream is comprised of a recycled hydrogen stream and a makeup hydrogen stream.

6. The process of claim 1, wherein the hydrogen stream comprises at least 70% hydrogen by weight.

7. The process of claim 1, wherein the catalyst is presented as a catalyst bed in the reactor.

8. The process of claim 7, wherein a portion of the hydrogen stream is fed to the catalyst bed in the reactor to quench the catalyst bed.

9. The process of claim 7, wherein the catalyst bed is comprised of two or more catalyst beds.

10. The process of claim 1, wherein the catalyst includes a support being at least one member of the group consisting of silica, alumina, and combinations thereof, and further includes an acidic component being at least one member of the group consisting of amorphous silica-alumina, zeolite, and combinations thereof.

11. The process of claim 10, wherein the catalyst includes an IUPAC Group 8-10 metal being at least one member of the group consisting of iron, cobalt, and nickel, and combinations thereof and further includes an IUPAC Group 6 metal being at least one member of the group consisting of molybdenum and tungsten, and combinations thereof.

12. The process of claim 11, wherein the IUPAC 8-10 metal is 2 to 20 percent by weight of the catalyst and the IUPAC Group 6 metal is 1 to 25 percent by weight of the catalyst.

13. The process of claim 1, wherein the catalyst is comprised of nickel, molybdenum, ultrastable Y-type zeolite, and γ-alumina support.

14. The process of claim 1, wherein specific reaction conditions include an operating temperature of the reactor being in the range of 200 to 450° C.

15. The process of claim 14, wherein the operating temperature of the reactor is about 300° C.

16. The process of claim 14, wherein the operating temperature of the reactor is about 350° C.

17. The process of claim 1, wherein specific reaction conditions include an hydrogen partial pressure of the reactor being in the range of 5 to 50 bar gauge.

18. The process of claim 17, wherein the hydrogen partial pressure of the reactor is less than 20 bar gauge.

19. The process of claim 1, wherein specific reaction conditions include a feed rate of the hydrogen stream being in the range of 500 to 5000 standard cubic feet per barrel of feedstock.

20. The process of claim 1, wherein the downstream process is a para-xylene recovery process.

21. The process of claim 1, further comprising:
supplying, to the reactor, a recycled hydrocarbon stream containing unreacted alkyl-bridged non-condensed alkyl multi-aromatic compounds.

22. The process of claim 21, wherein the recycled hydrocarbon stream is combined with the feed stream to form a combined feed stream being supplied to the reactor.

23. The process of claim 22, wherein the hydrogen stream is combined with the combined feed stream to form a second combined stream being supplied to the reactor.

24. The process of claim 1, further comprising:
supplying the product stream to a separation zone to separate the product into a lighter hydrocarbon stream and a heavier hydrocarbon stream.

25. The process of claim 24, wherein the lighter hydrocarbon stream is processed to provide a recycled hydrogen stream.

26. The process of claim 25, wherein the recycled hydrogen stream is combined with a makeup hydrogen stream to provide the hydrogen stream for supplying to the reactor.

27. The process of claim 1, wherein the downstream process further comprises:
supplying the product stream to a first separator to provide a first light stream and a first heavy stream; and
supplying the first light stream to a second separator to provide a second light stream and a second heavy stream;
wherein the first heavy stream and the second heavy stream are combined to form a heavier hydrocarbon stream.

28. The process of claim 27, wherein the downstream process further comprises:
supplying the heavier hydrocarbon stream to a fractionation zone for fractionating into two or more streams.

29. The process of claim 27, wherein the downstream process further comprises
supplying the heavier hydrocarbon stream to a first fractionator for fractionating into a first light fractionation stream and a first heavy fractionation stream, wherein at least a portion of the first light fractionation stream is supplied to a xylene processing unit; and
supplying the first heavy fractionation stream to a second fractionator for fractionating into a second light fractionation stream and a second heavy fractionation stream, wherein the second light fractionation stream is supplied to the xylene processing unit, and at least a portion of the second heavy fractionation stream is recycled to the reactor.

* * * * *